United States Patent [19]

Niira et al.

[11] Patent Number: 5,556,699
[45] Date of Patent: Sep. 17, 1996

[54] ANTIBIOTIC ZEOLITE-CONTAINING FILM

[75] Inventors: Reiji Niira, deceased, late of Kokubunki, by Yuriko Niira, Kiyotaka Niira, Hideaki Niira, legal heirs; Tatuo Yamamoto, Inazawa; Masashi Uchida, Nagoya, all of Japan

[73] Assignees: Shingawa Fuel Co. Ltd.; Shinanen New Ceramic Corporation, both of Japan

[21] Appl. No.: 461,165

[22] Filed: Jun. 5, 1995

Related U.S. Application Data

[63] Continuation of Ser. No. 996,490, Dec. 23, 1992, abandoned, which is a continuation of Ser. No. 210,820, Jun. 24, 1988, abandoned.

[30] Foreign Application Priority Data

Jun. 30, 1987 [JP] Japan .................................. 62-162710

[51] Int. Cl.$^6$ .................................................... B01D 39/08
[52] U.S. Cl. ........................ 428/323; 428/332; 428/334; 428/340; 428/328; 523/122; 523/220; 524/450
[58] Field of Search .................................... 428/323, 904; 524/450; 523/122, 220, 108; 252/102, 135; 430/221; 34/15

[56] References Cited

U.S. PATENT DOCUMENTS

| | | | |
|---|---|---|---|
| 4,775,585 | 10/1988 | Hagiwara et al. | 428/323 |
| 4,911,898 | 3/1990 | Hagiwara et al. | 423/118 |
| 4,911,899 | 3/1990 | Hagiwara et al. | 423/118 |
| 4,938,955 | 7/1990 | Niira et al. | 424/79 |
| 4,938,958 | 7/1990 | Niira et al. | 424/79 |
| 5,047,448 | 9/1991 | Tanaka et al. | 523/122 |
| 5,094,847 | 3/1992 | Yazaki et al. | 424/618 |
| 5,180,402 | 1/1993 | Kubota et al. | 8/490 |
| 5,208,016 | 5/1993 | Ohmae et al. | 424/78.27 |
| 5,433,424 | 7/1995 | Watanabe | 524/322 |
| 5,436,282 | 7/1995 | Gustafsson et al. | 523/102 |

FOREIGN PATENT DOCUMENTS

| | | |
|---|---|---|
| 13-4422 | 8/1938 | Japan . |
| 52-92000 | 8/1977 | Japan . |
| 55-38358 | 3/1980 | Japan . |
| 55-164236 | 12/1980 | Japan . |
| 57-77022 | 5/1982 | Japan . |
| 59-37956 | 1/1984 | Japan . |
| 59-133235 | 8/1984 | Japan . |
| 60-64611 | 4/1985 | Japan . |
| 60-79433 | 6/1985 | Japan . |
| 60-100504 | 6/1985 | Japan . |
| 60-184325 | 9/1985 | Japan . |
| 60-181002 | 9/1985 | Japan . |
| 60-178810 | 9/1985 | Japan . |
| 60-136795 | 9/1985 | Japan . |
| 60-136796 | 9/1985 | Japan . |
| 60-181370 | 9/1985 | Japan . |
| 60-174707 | 9/1985 | Japan . |
| 60-202162 | 10/1985 | Japan . |
| 61-138658 | 6/1986 | Japan . |
| 61-138795 | 6/1986 | Japan . |
| 61-138647 | 6/1986 | Japan . |
| 61-137564 | 6/1986 | Japan . |
| 61-103401 | 7/1986 | Japan . |
| 61-232253 | 10/1986 | Japan . |
| 62-7746 | 1/1987 | Japan . |
| 62-7747 | 1/1987 | Japan . |
| 62-7748 | 1/1987 | Japan . |
| 62-41775 | 2/1987 | Japan . |
| 62-70221 | 3/1987 | Japan . |
| 62-195038 | 8/1987 | Japan . |
| 62-195037 | 8/1987 | Japan . |
| 62-238900 | 10/1987 | Japan . |
| 62-241939 | 10/1987 | Japan . |
| 62-243665 | 10/1987 | Japan . |
| 62-241932 | 10/1987 | Japan . |

*Primary Examiner*—Patrick Ryan
*Assistant Examiner*—J. M. Gray
*Attorney, Agent, or Firm*—Graham & James LLP

[57] ABSTRACT

An antibiotic film comprises at least one organic polymeric film containing antibiotic zeolite, in which the content of the antibiotic zeolite is 10 to 100 mg per 1 m$^2$ of the organic polymeric film and the thickness of the organic polymeric film is not more than 15 microns and an antibiotic laminated film comprises a substrate, at least one side of which is laminated with the aforementioned antibiotic film. These films exhibit excellent antibiotic action although they contain rather small amount of antibiotic zeolite and the films also exhibit high transparency. These films can be used as materials for packaging foods, medical equipments and accessories and the like.

16 Claims, No Drawings

ANTIBIOTIC ZEOLITE-CONTAINING FILM

This is a continuation of application Ser. No. 07/996,490, filed Dec. 23, 1992, abandoned, which is a continuation of application Ser. No. 07/210,820, filed Jun. 24, 1988, abandoned.

BACKGROUND OF THE INVENTION

1. Field of the Invention

The present invention relates to an antibiotic zeolite-containing film and more particularly to an antibiotic zeolite-containing film exhibiting satisfactory antibiotic action although it contains a relatively small amount of antibiotic zeolite and having a high transparency as well as an antibiotic laminated film comprised of a substrate, at least one side of which is laminated with such antibiotic zeolite-containing film(s).

2. Description of the Prior Art

There have been known so-called antibiotic zeolites comprised of zeolites carrying antibiotic metals such as silver, copper and zinc (see, for instance, Japanese Patent Publication for Opposition Purpose (hereinafter referred to as "J. P. KOKOKU") No. 61-22977 and Japanese Patent Unexamined Publication (hereinafter referred to as "J. P. KOKAI") No. 60-181002). Moreover, it is also known that such a zeolite can be incorporated into materials such as resins to impart antibiotic action to such materials (see, for instance, J. P. KOKAI No. 59-133235).

However, the antibiotic zeolites are rather expensive. Therefore, it is necessary, from a practical point of view, to impart sufficient antibiotic action to resins while using the antibiotic zeolite as small amounts as possible. However, in the method disclosed in J. P. KOKAI No. 59-133235, the antibiotic zeolite is dispersed in whole the molded resin products, which leads to the formation of very expensive antibiotic resin products.

There is another problem, concerning the use of the antibiotic zeolite in materials such as resins, that the resins or the like tends to cause the reduction in their transparency if the antibiotic zeolite is used in an amount greater than a certain limit. Therefore, a relatively thick film obtained by simply forming a resin admixed with such antibiotic zeolite into a film exhibits low transparency and the commercial value thereof as a transparent film also becomes low.

SUMMARY OF THE INVENTION

Accordingly, it is a purpose of the present invention to provide an antibiotic zeolite-containing film having a relatively low content of antibiotic zeolite, which exhibits a satisfactory antibiotic action and transparency comparable to that of the conventional antibiotic films.

It is another purpose of the present invention to provide an antibiotic laminated film comprises a substrate, at least one side of which is laminated with such an antibiotic film.

Thus, according to an aspect of the present invention, an antibiotic film is provided and the film comprises an organic polymeric film containing at least one antibiotic zeolite, the content of the antibiotic zeolite being in the range of from 10 to 100 mg per 1 $m^2$ of the organic polymeric film and the thickness of the film being not more than 15 microns.

According to another aspect of this invention, there is provided an antibiotic laminated film which comprises a substrate, at least one side of which is laminated with an organic polymeric film containing at least one antibiotic zeolite, the content of the antibiotic zeolite being in the range of from 10 to 100 mg per 1 $m^2$ of the organic polymeric film and the thickness of the film being not more than 15 microns.

DETAILED EXPLANATION OF THE INVENTION

The present invention will hereunder be explained in more detail.

The "antibiotic zeolites" used in the invention are those of which ion-exchangeable ions are partially or completely ion-exchanged with antibiotic ions. Examples of such antibiotic ions are silver, copper, zinc, mercury, tin, lead, bismuth, cadmium, chromium and thallium ions. Preferred antibiotic metal ions are silver, copper and zinc ions. These ions may be used alone or in combination. It is also preferred to use, as such antibiotic zeolite, those further ion-exchanged with ammonium ions in addition to the foregoing antibiotic metal ions in order to effectively prevent discoloration of resins into which antibiotic zeolites are incorporated.

In the antibiotic film of this invention, either natural or synthetic zeolites may be used as the "zeolite component". Zeolites are in general aluminosilicate having a three dimensional skeletal structure represented by the following formula: $XM_{2/n}$-$Al_2O_3$-$YSiO_2$-$ZH_2O$. In the general formula, M represents an ion-exchangeable ion and in general a monovalent or divalent metal ion, n represents atomic valency of the (metal) ion, X and Y represent coefficients of metal oxide and silica respectively, and Z represents the number of water of crystallization.

Examples of such zeolites include A-type zeolites, X-type zeolites, Y-type zeolites, T-type zeolites, high-silica zeolites, sodalite, mordenite, analcite, clinoptilolite, chabazite and erionite. However, it should be appreciated that the present invention is not restricted to these specific examples. The ion-exchange capacities of these exemplified zeolites are as follows: A-type zeolite=7 meq./g; X-type zeolite=6.4 meq./g; Y-type zeolite=5 meq./g; T-type zeolite=3.4 meq./g; sodalite=11.5 meq./g; mordenite=2.6 meq./g; analcite=5 meq./g; clinoptilolite=2.6 meq./g; chabazite=5 meq./g; and erionite=3.8 meq./g. Thus, all the zeolites listed above have ion-exchange capacities sufficient to undergo ion-exchange with antibiotic metal and ammonium ions and these zeolites may be used alone or in combination in the antibiotic films.

As already mentioned above, the antibiotic zeolites as used herein are those of which ion-exchangeable ions such as sodium ions, potassium ions, calcium ions, magnesium ions and iron ions are partially or completely ion-exchanged with the aforementioned antibiotic metal ions such as silver, copper or zinc ions and/or ammonium ions.

From the viewpoint of antibiotic effect, the antibiotic metal ions are in general contained in the zeolite in an amount preferably ranging from 0.1 to 15% on the basis of the weight of the zeolite. In the present invention, the content of silver ions in the zeolite ranges from 0.1 to 15%, preferably 0.1 to 5%; and that of copper and zinc ions are preferably 0.1 to 8% respectively in order to impart an effective antibiotic action to the zeolite. On the other hand, the content of ammonium ions in zeolite ranges from 0.5 to 5%, preferably 0.5 to 2% in order to effectively prevent the discoloration of resins into which the antibiotic zeolites are incorporated. In this respect, the term "%" herein means "% by weight" expressed in the weight of the zeolite weighed after drying at a temperature of 110° C.

In the antibiotic films of this invention, it is particularly preferred to use antibiotic zeolites of which ion-exchangeable ions are partially or completely exchanged with ammonium and silver ions or further either or both of copper and zinc ions.

Methods for preparing such antibiotic zeolites employed in this invention will now be detailed below.

The antibiotic zeolite used in the antibiotic film of this invention may be obtained by bringing zeolite into contact with a previously prepared aqueous mixed solution containing antibiotic metal ions such as silver, copper and zinc ions and optionally ammonium ions to cause ion-exchange between ion-exchangeable ions present in zeolite and the aforesaid antibiotic metal ions. The contact between these ions may be carried out according to a batch technique or a continuous technique (such as a column method) at a temperature of from 10° to 70° C., preferably 40° to 60° C., for 3 to 24 hours, preferably 10 to 24 hours. During the contact, the pH value of the aqueous mixed solution is adjusted to 3 to 10, preferably 5 to 7 in order to prevent silver oxide and the like from causing deposition on the surface of the zeolite or within pores thereof. In addition, each of the ion species is generally used in the form of a salt to prepare the aqueous mixed solution.

For instance, there may be mentioned such an ammonium ion source as ammonium nitrate, ammonium sulfate and ammonium acetate; such a silver ion source as silver nitrate, silver sulfate, silver perchlorate, silver acetate and diamine silver nitrate; such a copper ion source as copper(II) nitrate, copper sulfate, copper perchlorate, copper acetate and tetracyan copper potassium; such a zinc ion source as zinc(II) nitrate, zinc perchlorate, zinc acetate and zinc thiocyanate; such a mercury ion source as mercury perchlorate, mercury nitrate and mercury acetate; such a tin ion source as tin sulfate; such a lead ion source as lead sulfate and lead nitrate; such a bismuth ion source as bismuth chloride and bismuth iodide; such a cadmium ion source as cadmium perchlorate, cadmium sulfate, cadmium nitrate and cadmium acetate; such a chromium ion source as chromium perchlorate, chromium sulfate, chromium ammonium sulfate and chromium acetate; and such a thallium ion source as thallium perchlorate, thallium sulfate, thallium nitrate and thallium acetate.

The content of such ions as ammonium ions in the antibiotic zeolites may appropriately be controlled by adjusting the concentration of each ion species (or salt) in the aforesaid aqueous mixed solution. For instance, if the antibiotic zeolite comprises ammonium and silver ions, the antibiotic zeolite having an ammonium ion content of 0.5 to 5% and a silver ion content of 0.1 to 5% can appropriately be obtained by bringing zeolite into contact with an aqueous mixed solution having an ammonium ion concentration of 0.85 to 3.1 mole/l and a silver ion concentration of 0.002 to 0.15 mole/l. If the antibiotic zeolite further comprises copper and/or zinc ions, the antibiotic zeolite having copper and/or zinc ion contents of 0.1 to 8%, respectively, can appropriately be prepared by employing an aqueous mixed solution containing 0.1 to 0.85 mole/l of copper ions and/or 0.15 to 1.2 mole/l of zinc ions in addition to the foregoing amount of ammonium and silver ions.

Alternatively, the antibiotic zeolites used in the present invention may also be prepared by using separate aqueous solutions each containing single ion species (or salt) and bringing zeolite into contact with each solution one by one to cause ion-exchange therebetween. The concentration of each ion species in a specific solution can be determined in accordance with the concentrations of those ion species in the aforementioned aqueous mixed solutions.

After the ion-exchange treatment, the resultant antibiotic zeolites are washed with water sufficiently followed by drying. The drying is very important to obtain pinhole-free antibiotic films as final products. Therefore, the antibiotic zeolites thus prepared should be dried under conditions such that the zeolite never causes evaporation or elimination of water during forming resins admixed with the antibiotic zeolite into antibiotic films. For example, it is preferable to dry the antibiotic zeolites till the residual moisture content in the zeolite reaches about 3 to 5%. For that purpose, it is desirable to dry the zeolite at about 100° to 400° C., preferably about 150° to 250° C. under normal pressure, or at 50° to 250° C., preferably 100° to 200° C. under a reduced pressure (e.g., about 1 to 30 torr).

After drying, the antibiotic zeolites thus obtained are pulverized and classified and then are incorporated into a desired resin. In this respect, the average particle size of the antibiotic zeolites are not more than 6 microns, preferably 0.3 to 4 microns and more preferably 0.5 to 2 microns for the purpose of obtaining an antibiotic film having high antibiotic action.

In the present invention, the organic polymeric materials used for forming antibiotic films may be any organic polymers so far as they can be formed into films. Examples of such organic polymeric materials include ionomer resins, EEA resins, EVA resins, vinyl chloride resins, chlorinated polyethylene, fluorine resins, polyamide resins, thermoplastic polyurethane elastomers, polyethers, ether ketone resins, polysulfone resins, high density polyethyelenes, low density polyethylenes, linear low density polyethylenes, polycarbonate resins, butadiene resins, polypropylene resins, styrene type specific transparent resins, polyacrylate resins, reinforced polyethylene terephthalate resins, polystyrene, vinylidene chloride resins, conductive resins (such as those manufactured and sold by SHOWA DENKO K.K. under the trade name of SHOWSTAT), silicone resins, ABS resins, AS resins, polyesters, nylons, polyacetals, polyvinyl alcohols, polycarbonates, acrylic resins, phenolic resins, melamine resins, unsaturated polyester resins, epoxy resins, urethane resins, urea resins, rayon, cuprammonium rayons and natural and synthetic rubbers.

The antibiotic films of the present invention can be produced by admixing the antibiotic zeolite and an organic polymeric compound in a usual manner and then molding the mixture obtained (forming it into films). The formation of the film can be carried out according to any known methods such as casting method, extrusion methods (e.g., inflation method, T-die method, calendering method, cutting method) and drawing method. For instance, in the casting method, resin flakes as a starting material are dissolved in water or an organic solvent and then antibiotic zeolites and optionally additives such as plasticizers and discoloration inhibitors are added to the resultant solution. Then, the resulting mixture is filtered and defoamed before casting the mixture on a rotatable flat metal support to obtain a thin film.

The thickness of the antibiotic film of the invention is suitably not more than 15 microns, preferably 2 to 12 microns and more preferably 3 to 6 microns. In addition, the content of the antibiotic zeolites in the antibiotic film ranges from 10 to 100 mg, preferably 25 to 75 mg per 1 $m^2$ of the organic polymeric film. This is because the antibiotic film obtained from the organic polymeric material containing the antibiotic zeolite in an amount defined by the foregoing range certainly exhibits a desired transparency.

The present invention further relates to an antibiotic laminated film comprised of a substrate, one or both sides of which are laminated with the aforementioned antibiotic film of the invention.

The substrate may be, for instance, resin films. Examples of such resin films are those comprised of organic polymeric materials listed above as the materials for forming the antibiotic films. The thickness thereof may vary according to various conditions such as its applications and the strength thereof. However, it is in general 5 to 100 microns, preferably 10 to 50 microns.

Examples of methods for laminating the substrate with the antibiotic film(s) include co-extrusion method and laminating method.

The antibiotic film and the antibiotic laminated film may further include at least one discoloration inhibitor which may be any compounds known as ultraviolet absorbers, antioxidants, light stabilizers, ultraviolet stabilizers, processing stabilizers, metal deactivators or fluorescent whiteners.

As such discoloration inhibitors, it is possible to use at least one member selected from the group consisting of, for instance, benzotriazole type compounds, oxalic acid anilide type compounds, salicylic acid type compounds, cyanoacrylate type compounds, benzophenone type compounds, hindered amine type compounds, hindered phenol type compounds, phosphorus type compounds, sulfur type compounds and hydrazine type compounds.

Examples of the benzotriazole type compounds are 2-(5-methyl-2-hydroxyphenyl)-benzotriazole, 2-(2-hydroxy-3,5-bis(alpha,alpha-dimethylbenzyl)-phenyl)-2H-benzotriazole, 2-(3,5-di-tert-butyl-2-hydroxyphenyl)-benzotriazole, 2-(3-tert-butyl-5-methyl-2-hydroxyphenyl)-5-chlorobenzotriazole, 2-(3,5-di-tert-butyl-2-hydroxyphenyl)-5-chlorobenzotriazole and 2-(3,5-di-tert-amyl-2-hydroxyphenyl)-benzotriazole.

Examples of the oxalic acid anilide type compounds are 2-ethoxy-2'-ethyloxalic acid bisanilide and 2-ethoxy-5-tert-butyl-2'-ethyloxalic acid bisanilide.

Examples of the salicylic acid type compounds are phenyl salicylate, p-tert-butylphenyl salicylate and p-octylphenyl salicylate.

Examples of the cyanoacrylate type compounds are 2-ethylhexyl-2-cyano-3,3'-diphenyl acrylate and ethyl-2-cyano-3,3'-diphenyl acrylate.

Examples of the benzophenone type compounds are 2,4-dihydroxybenzophenone, 2-hydroxy-4-methoxybenzophenone, 2-hydroxy-4-octoxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methoxy-5-sulfobenzophenone.

Examples of the hindered amine type compounds are dimethyl succinate-1-(2-hydroxyethyl)-4-hydroxy-2,2,6,6-tetramethylpiperidine polycondensate, poly((6-(1,1,3,3-tetramethylbutyl)-imino-1,3,5-triazine-2,4-diyl) ((2,2,6,6-tetramethyl-4-piperidyl)-imino)-hexamethylene-((2,2,6,6-tetramethyl-4-piperidyl)-imino)); and bis(1,2,2,6,6-pentamethyl-4-piperidyl)-2-(3,5-di-tert-butyl-4-hydroxybenzyl)-2-n-butylmalonate.

Examples of the hindered phenol type compounds are triethylene glycol bis(3-(3-tert-butyl-5-methyl-4-hydroxyphenyl)-propionate), 1,6-hexanediol bis(3-(3,5-di-tert-butyl-4-hydroxyphenyl)-propionate), 2,4-bis(n-octylthio)-6-(4-hydroxy-3,5-di-tert-butylanilino)-1,3,5-triazine, pentaerythritol tetrakis(3-(3,5-di-tert-butyl-4-hydroxyphenyl)-propionate), 2,2-thiodiethylene-bis(3-(3,5-di-tert-butyl-4-hydroxyphenyl)-propionate), octadecyl 3-(3,5-di-tert-butyl-4-hydroxyphenyl)-propionate, 2,2-thiobis(4-methyl-6-tert-butylphenol), N,N'-hexamethylenebis(3,5-di-tert-butyl-4-hydroxy-hydrocinnamamide), 3,5-di-tert-butyl-4-hydroxy-benzylphosphonate diethyl ester, 1,3,5-trimethyl-2,4,6-tris(3,5-di-tert-butyl-4-hydroxybenzyl)benzene, calcium (ethyl-bis(3,5-di-tert-butyl-4-hydroxybenzyl-phosphonate)) and tris(3,5-di-tert-butyl-4-hydroxybenzyl) isocyanurate.

Examples of the phosphorus type compounds are triphenyl phosphite, tris(nonylphenyl) phosphite, tris(2-ethylhexyl) phosphite, tridecyl phosphite, tris(tridecyl) phosphite, diphenyl mono(2-ethylhexyl) phosphite, diphenyl monodecyl phosphite, diphenyl monotridecyl phosphite, tetraphenyl tetra(tridecyl)-pentaerythritol tetraphosphite, tetra(tridecyl)-4,4'-isopropylidene diphenylphosphite, bis(tridecyl)-pentaerythritol diphosphite, distearylpentaerythritol diphosphite and tris(2,4-di-tert-butylphenyl) phosphite.

Examples of the sulfur type compounds are dilaurylthio dipropionate, dimyristylthio dipropionate and distearylthio dipropionate.

Examples of the hydradine type compounds are N,N'-bis(3-(3,5-di-tert-butyl-4-hydroxyphenyl)-propionyl)hydradine.

These discoloration inhibitors may be used alone or in combination in the film of this invention. These discoloration inhibitors may be added to the antibiotic film and the antibiotic laminated film of the present invention in an amount of 0.001 to 1.0% on the basis of the weight of the organic polymeric material.

The antibiotic film thus prepared and the antibiotic laminated film obtained by laminating a substrate with such antibiotic film(s) of this invention exhibit excellent antibiotic action and high transparency.

Since the antibiotic film has a thickness of not more than 15 microns, the antibiotic film per se may be used as a packaging material such as the packaging material for foods and medical goods (such as equipments or accessories). Moreover, it is also possible to impart antibiotic properties to other materials by properly coating the materials with the antibiotic film of this invention.

On the other hand, the antibiotic laminated film of this invention generally has a thickness of 15 to 50 microns and high strength compared with the antibiotic film and, therefore, the laminated films are suitable to use as packaging materials and containers for foods, packaging materials for garments and packaging materials for medical use, for instance, materials for medical equipments and accessories.

The antibiotic laminated film of this invention may further be laminated with a layer of other materials such as resins, metals and paper to form sheets or other molded products. Examples of the products include brushes and products used in the mouth such as a tooth brush, an artificial tooth, a substrate for an artificial tooth and filler used for tooth.

As discussed above in detail, the antibiotic film and the antibiotic sheet (antibiotic laminated film) of the present invention exhibit excellent antibiotic action although they contain rather small amount of the antibiotic zeolite. The antibiotic film and the antibiotic sheet of the present invention are particularly effective to the following bacteria, fungi and yeast: *Bacillus cereus var mycoides, Escherchia coli, Pseudomonas aeruginosa, Staphylococcus aureus, Streptococcus feacalis, Salmonella gallinarum, Vibrio parahaemdyticus, Candida albicans, Streptococcus mutans,*

*Legionella pneumophila, Fuso bacterium, Aspergillus niger, Aureobasidium pullulans, Cheatomium globosum, Gliocladium virens, Pencillum funiculosum* and *Saccharomyces cerevisiae.*

The present invention will be described in more detail with reference to the following non-limitative working examples and reference examples. In addition, the effects practically achieved will be discussed in comparison with Comparative Example.

REFERENCE EXAMPLE (Preparation of Antibiotic Zeolite)

Powder of A-type zeolite (1 kg; $Na_2O$-$Al_2O_3$-$1.9SiO_2$-$XH_2O$; average particle size=1.5 microns) which had been dried under heating at 110° C. was added to water to form 1.3 liters of slurry thereof. Then the slurry was stirred to degassify, proper amount of 0.5N nitric acid solution and water were added thereto to adjust pH to 5 to 7 and to thus obtain a slurry of a total volume of 1.8 liters. Thereafter, ion exchange was carried out by adding, to the slurry, 3 liters of a mixed aqueous solution containing 1.05 mole/l of $NH_4NO_3$, 0.068 mole/l of $AgNO_3$ and 0.4 mole/l of $Zn(NO_3)_2$ to obtain a slurry having a total volume of 4.8 liters and maintaining the slurry at a temperature of 40° to 60° C. for 10 to 24 hours while stirring to hold the slurry at the equilibrium state. After the ion-exchange, the zeolite phase was filtered off followed by washing with water at room temperature or warm water until almost no excess silver and zinc ions remained in the zeolite phase. Then, the zeolite sample thus obtained was dried at 200° C. under 1 torr to recover antibiotic zeolite. The antibiotic zeolite thus obtained included 2% Ag, 5% Zn, and 4% $NH_4$.

EXAMPLE 1

Antibiotic films of 4, 10, 18 and 44 microns thick respectively were prepared by adding, to vinylidene chloride resin (manufactured and sold by Kureha Chemical Industry Co., Ltd.), the antibiotic zeolite obtained in Reference Example in the amount equal to 10, 25, 50 and 100 mg per 1 $m^2$ of the resin, respectively and then extruding the resin by T-die method (operation condition: extrusion temperature=200° C.). The antibiotic action of the resultant antibiotic films was estimated as follows:

The antibiotic action was determined using *Escherichia coli* IFO 3301 as a test strain. The bacterial cell dispersion of the *E. coli* was prepared by culturing *E. coli* strain on a normal bouillon culture medium at 37° C. over night and then diluting the culture medium with sterilized saline so that the number of cells per 1 ml equals to $10^4$ to $10^5$. Test pieces (antibiotic film) were washed with ether and were sprayed with a given amount of the bacterial cell dispersion prepared above followed by maintaining the test pieces at 37° C. for 24 hours. The viable cells on the test pieces were washed off with 20 ml of sterilized saline, 1 ml of the wash liquid was diluted with sterilized saline by 50 times and 1 ml of the diluted wash liquid was dropped on a test paper for the family of *E. coli* strains (manufactured and sold by Shibata Experimental Instruments Industries Co., Ltd.; 8051-301). These test paper were cultured at 35° to 37° C. for 24 hours in an isothermal device (manufactured and sold by the same company; 8051-31).

The antibiotic action of the test pieces were estimated and the results were expressed in 5-rank estimation on the basis of the presence or absence of red spots and the number thereof. The results are summarized in Table I. A film free of the antibiotic zeolite was likewise prepared and the antibiotic action thereof was also examined.

TABLE I

| Amount of Antibiotic Zeolite Added (mg/$m^2$) | Thickness of the Film (micron) | | | |
| --- | --- | --- | --- | --- |
| | 4 | 10 | 18 | 44 |
| 0 | 1 | 1 | 1 | 1 |
| 10 | 3 | 2 | 1 | 1 |
| 25 | 5 | 3 | 2 | 1 |
| 50 | 5 | 5 | 3 | 1 |
| 100 | 5 | 5 | 3 | 2 |

Estimation Ranks:
Rank 5: No bacterial cell was detected;
Rank 4: The number of red spots = 2 to 3;
Rank 3: There was observed not more than several % of the bacterial cell number present in the bacterial cell dispersion for the test;
Rank 2: There was observed 5 to 50% of the bactertial cell number present in the bacterial cell dispersion for the test;
Rank 1: There was observed not less than 50% of the bacterial cell number present in the bacterial cell dispersion for the test.

EXAMPLE 2

Antibiotic sheets having a thickness of 30 microns were prepared by co-extruding low density polyethylene (manufactured and sold by MITSUBISHI CHEMICAL INDUSTRIES LTD. under the trade name of NOVATEC-L grade F161), into which the antibiotic zeolite prepared in Reference Example was incorporated in the amount equal to 10, 25, 50 and 100 mg/$m^2$ respectively, and the same low density polyethylene free of the antibiotic zeolite (operation condition: extrusion temperature=260° C.) to laminate these polymers. In this respect, the thickness of the polyethylene (first layer) containing the antibiotic zeolite and the polyethylene free of the antibiotic zeolite (second layer) was adjusted to 3 microns/27 microns (Sheet A); 10 microns/20 microns (Sheet B); 20 microns/10 microns (Sheet C); and 27 microns/3 microns (Sheet D), respectively. The antibiotic action of the resultant sheets was examined in the same manner as in Example 1 and the results observed were listed in Table II.

TABLE II

| Amount of Anitbiotic Zeolite Added (mg/$m^2$) | Sheet Number | | | |
| --- | --- | --- | --- | --- |
| | A | B | C | D |
| 0 | 1 | 1 | 1 | 1 |
| 10 | 4 | 1 | 1 | 1 |
| 25 | 5 | 3 | 2 | 1 |
| 50 | 5 | 4 | 3 | 1 |
| 100 | 5 | 5 | 5 | 3 |

Estimation Ranks:
Rank 5: No bacterial cell was detected;
Rank 4: The number of red spots = 2 to 3;
Rank 3: There was observed not more than several % of the bacterial cell number present in the bacterial cell dispersion for the test;
Rank 2: There was observed 5 to 50% of the bactertial cell number present in the bacterial cell dispersion for the test;
Rank 1: There was observed not less than 50% of the bacterial cell number present in the bacterial cell dispersion for the test.

EXAMPLE 3

Antibiotic zeolites were prepared in the same manner as in Reference Example except that A-type zeolites having average particle size of 0.5, 2.4, 5.2 and 11 microns respectively were used instead of the A-type zeolite having an average particle size of 1.5 microns. Antibiotic films having a thickness of 10 microns were prepared in the same manner as in Example 1 and the antibiotic action of the resultant antibiotic films was estimated according in the same manner as in Example 1. The results observed are summarized in Table III.

TABLE III

| Added Amount of | Average Particle Size (micron) | | | | |
|---|---|---|---|---|---|
| Antibiotic Zeolite (mg/m$^2$) | 0.5 | 1.5 | 2.4 | 5.2 | 11 |
| 50 | 5 | 5 | 5 | 5 | 4 |

Estimation Ranks:
Rank 5: No bacterial cell was detected;
Rank 4: The number of red spots = 2 to 3;
Rank 3: There was observed not more than several % of the bacterial cell number present in the bacterial cell dispersion for the test;
Rank 2: There was observed 5 to 50% of the bactertial cell number present in the bacterial cell dispersion for the test;
Rank 1: There was observed not less than 50% of the bacterial cell number present in the bacterial cell dispersion for the test.

EXAMPLE 4

5 parts by weight of the antibiotic zeolite obtained in Reference Example was mixed with 100 parts by weight of polyurethane resin (Nippon Zeon Co., Ltd. RA-80). The resulting mixture was coated on a substrate used for a brush (15×150×8 mm) with eighty holes for filling (15. mm in diameter×3 mm in depth) in thickness of 10 microns and dried at a temperature of 120° C. for 1 minutes to form a film. The film contained 50 mg of the antibiotic zeolite per 1 m$^2$. Four fillings (1 mm in diameter×25 mm in length) made up of nylon 6 (Mitsubishi Chemical Industries, Ltd, Novamid 1010C2) were filled in each holes to form a tooth brush (No.1).

The antibiotic activity of the tooth brush coated with antibiotic zeolite-containing film was estimated. The estimation was conducted by immersing the brush in a aqueous solution containing *Pseudomonas aureus* ($10^5$/ml) and the change of the number of *Pseudomonas aureus* with time was measured. The result is shown in Table IV. The antibiotic activity of a tooth brush not coated with the film (No.2) was also examined.

TABLE IV

| Brush No. | 0 hr | 10 hrs | 24 hrs | 36 hrs | 48 hrs |
|---|---|---|---|---|---|
| 1 | $1 \times 10^5$ | $3 \times 10$ | 0 | 0 | 0 |
| 2 (blank) | $1 \times 10^5$ | $4 \times 10^5$ | $6 \times 10^6$ | $2 \times 10^7$ | $10^8 <$ |

EXAMPLE 5

3 parts by weight of the antibiotic zeolite obtained in Reference Example and 100 parts by weight of acrylonitrile-butadiene copolymer pellets (Mitsubishi Monsant Co,. Ltd., Toughlex YT-735) were mixed and the resulting mixture and nylon 6 (Ube Industries, Ltd., 1030B) were co-extruded to form a laminated sheet (No.1). The thickness of the antibiotic zeolite-containing ABS resin layer is 15 microns and that of nylon layer is 50 microns.

According to the same manner, a laminated sheet (No. 2) comprising ABS resin layer and nylon layer was prepared, provide that the ABS resin layer contained no antibiotic zeolite.

Aqueous solutions containing $10^5$/ml of *Candida albicans, Streptococcus mutans* or *Pseudomonas aeruginosa* were prepared and 1 ml of the solution was sprayed on the laminated sheet. Then the sheet was kept at a temperature of 37° C. and at humidity of 95% or more for 18 hours and then the number of bacteria on the sheet was measured. The results are listed in Table V.

TABLE V

| Sheet No. | Bateria | 0 hr | 18 hrs |
|---|---|---|---|
| 1 | *Candida albicans* | $1 \times 10^5$ | 0 |
|  | *Streptococcus mutans* | $1 \times 10^5$ | 0 |
|  | *Pseudomonas aerguinosa* | $1 \times 10^5$ | 0 |
| 2 | *Candida albicans* | $1 \times 10^5$ | $3 \times 10^5$ |
|  | *Streptococcus mutans* | $1 \times 10^5$ | $7 \times 10^4$ |
|  | *Pseudomonas aeruginosa* | $1 \times 10^5$ | $4 \times 10^5$ |

What is claimed is:

1. A transparent self supporting antibiotic film comprising at least one organic polymeric film containing antibiotic zeolite, the content of the antibiotic zeolite being 25 to 100 mg per 1 m$^2$ of the organic polymeric film and the thickness of the organic polymeric film being not more than 10 microns, the antibiotic zeolite being selected from those of which ion-exchangeable ions are partially or completely ion-exchanged with antibiotic ions selected from the group consisting of silver, copper and zinc ions, and the antibiotic metal ions being contained in the zeolite in an amount ranging from 0.1 to 15% by weight on the basis of the weight of the zeolite; wherein antibiotic activity is fully effective and complete (100%).

2. An antibiotic film according to claim 1 wherein the content of the antibiotic zeolite is 25 to 75 mg per 1 m$^2$ of the organic polymeric film.

3. An antibiotic film according to claim 1 wherein the average particle size of the antibiotic zeolite is not more than 6 microns.

4. An antibiotic film according to claim 1 wherein the antibiotic zeolite is further ion-exchanged with ammonium ions.

5. An antibiotic film according to claim I wherein the antibiotic film further comprises at least one discoloration inhibitor selected from the group consisting of ultraviolet absorbers, antioxidants, light stabilizers, ultraviolet stabilizers, processing stabilizers, metal deactivators and fluorescent whiteners.

6. An antibiotic film according to claim 5 wherein the discoloration inhibitor is added to the antibiotic film in an amount of 0.001 to 1.0% by weight on the basis of the organic polymeric film.

7. A transparent antibiotic laminated film comprising a substrate, at least one side of which is laminated with an organic polymeric film containing antibiotic zeolite, the content of the antibiotic zeolite being 25 to 100 mg per 1 m$^2$ of the organic polymeric film and the thickness of the organic polymeric film being not more than 10 microns, the antibiotic zeolite being selected from those of which ion-exchangeable ions are partially or completely ion-exchanged with antibiotic ions selected from the group consisting of silver, copper and zinc ions, and the antibiotic metal ions being contained in the zeolite in an amount ranging from 0.1 to 15% by weight on the basis of the weight of the zeolite; wherein antibiotic activity is fully effective and complete (100%).

8. An antibiotic laminated film according to claim 7 wherein the substrate is a resin film.

9. An antibiotic laminated film according to claim 7 wherein the content of the antibiotic zeolite in the organic polymeric film is 25 to 75 mg per 1 m$^2$ of the organic polymeric film.

10. An antibiotic laminated film according to claim 7 wherein the average particle size of the antibiotic zeolite included in the organic polymeric film is not more than 6 microns.

11. An antibiotic laminated film according to claim 7 wherein the thickness of the antibiotic laminated film ranges from 5 to 100 microns.

12. An antibiotic laminated film according to claim 7 wherein the antibiotic zeolite is further ion-exchanged with ammonium ions.

13. An antibiotic laminated film according to claim 7 wherein the organic polymeric film further comprises at least one discoloration inhibitor selected from the group consisting of ultraviolet absorbers, antioxidants, light stabilizers, ultraviolet stabilizers, processing stabilizers, metal deactivators and fluorescent whiteners.

14. An antibiotic laminated film according to claim 13 wherein the discoloration inhibitor is added to the organic polymeric film in an amount of 0.001 to 1.0% by weight on the basis of the organic polymeric film.

15. A transparent self supporting antibiotic film comprising at least one organic polymeric film containing an antibiotic zeolite having a particle size of not more than 6 microns, the content of the antibiotic zeolite being 25 to 100 mg per 1 $m^2$ of the organic polymeric film and the thickness of the organic polymeric film being not more than 10 microns, the antibiotic zeolite being selected from those of which ion-exchangeable ions are partially or completely ion-exchanged with antibiotic ions selected from the group consisting of silver, copper and zinc ions, and the antibiotic metal ions being contained in the zeolite in an amount ranging from 0.1 to 15% by weight on the basis of the weight of the zeolite; wherein antibiotic activity is fully effective and complete (100%).

16. An antibiotic laminated film comprising a substrate, at least one side of which is laminated with the transparent antibiotic film according to claim 15.

* * * * *